US012788367B2

(12) United States Patent
Osawa

(10) Patent No.: US 12,788,367 B2
(45) Date of Patent: Nov. 10, 2026

(54) ULTRASOUND TRANSDUCER

(71) Applicant: FUJIFILM Corporation, Tokyo (JP)

(72) Inventor: Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 163 days.

(21) Appl. No.: 18/465,661

(22) Filed: Sep. 12, 2023

(65) Prior Publication Data

US 2023/0414200 A1 Dec. 28, 2023

Related U.S. Application Data

(63) Continuation of application No. PCT/JP2022/006899, filed on Feb. 21, 2022.

(30) Foreign Application Priority Data

Mar. 26, 2021 (JP) ................................ 2021-053464

(51) Int. Cl.
*A61B 8/00* (2006.01)
*B06B 1/06* (2006.01)

(52) U.S. Cl.
CPC .......... *A61B 8/4488* (2013.01); *B06B 1/0622* (2013.01); *B06B 1/067* (2013.01); *B06B 2201/76* (2013.01)

(58) Field of Classification Search
CPC ... A61B 8/4488; A61B 8/4281; A61B 8/4494; B06B 1/0622; B06B 1/067; B06B 2201/76; G01S 7/52079; G01S 15/8915; G10K 11/02; H04R 17/00
See application file for complete search history.

(56) References Cited

U.S. PATENT DOCUMENTS 5,886,454 A * 3/1999 Ito ........................ B06B 1/0622 310/326
6,225,729 B1 5/2001 Izumi et al.
2005/0122004 A1 6/2005 Shibamoto et al.
(Continued)

FOREIGN PATENT DOCUMENTS

EP 1542005 A1 6/2005
JP H11-155857 A 6/1999
(Continued)

OTHER PUBLICATIONS

The extended European search report issued by the European Patent Office on Jul. 3, 2024, which corresponds to European Patent Application No. 22774834.0, and is related to U.S. Appl. No. 18/465,661.
(Continued)

*Primary Examiner* — Kaitlyn E Sebastian
(74) *Attorney, Agent, or Firm* — Studebaker Brackett PLLC

(57) ABSTRACT

Provided is an ultrasound transducer 1 in which a plurality of piezoelectric elements (3) are arranged on a backing material along an arrangement direction, the ultrasound transducer (1) including a plurality of acoustic matching layers (4, 5, 6, 7) laminated on each piezoelectric element (3), in which at least one acoustic matching layer (4) among the plurality of acoustic matching layers (4, 5, 6, 7) consists of at least one acoustic matching piece (4A, 4B) having a width narrower than a width of the piezoelectric element (3) in the arrangement direction.

13 Claims, 6 Drawing Sheets

(56) References Cited

U.S. PATENT DOCUMENTS

| | | | | |
|---|---|---|---|---|
| 2010/0066207 | A1 | 3/2010 | Saito | |
| 2013/0090561 | A1 | 4/2013 | Kusukame et al. | |
| 2013/0195333 | A1 * | 8/2013 | Singh .................... | G03F 7/0035<br>310/334 |

FOREIGN PATENT DOCUMENTS

| | | | | |
|---|---|---|---|---|
| JP | 2005-64623 | A | | 3/2005 |
| JP | 2006270725 | A | * | 10/2006 |
| JP | 3926448 | B2 | | 6/2007 |
| JP | 2008307117 | A | | 12/2008 |
| JP | 2016-192666 | A | | 11/2016 |
| JP | 2020-175049 | A | | 10/2020 |

OTHER PUBLICATIONS

Communication pursuant to Article 94(3) EPC issued by the European Patent Office on Apr. 9, 2025, which corresponds to European Patent Application No. 22774834.0-1001 and is related to U.S. Appl. No. 18/465,661.

International Search Report issued in PCT/JP2022/006899; mailed May 17, 2022.

International Preliminary Report On Patentability (Chapter I) and Written Opinion of the International Searching Authority issued in PCT/JP2022/006899; issued Sep. 12, 2023.

“Notice of Reasons for Refusal” Office Action issued in JP 2023-508807; mailed by the Japanese Patent Office on Jan. 20, 2026.

* cited by examiner

ULTRASOUND TRANSDUCER

CROSS-REFERENCE TO RELATED APPLICATIONS

This application is a Continuation of PCT International Application No. PCT/JP2022/006899 filed on Feb. 21, 2022, which claims priority under 35 U.S.C. § 119(a) to Japanese Patent Application No. 2021-053464 filed on Mar. 26, 2021. The above applications are hereby expressly incorporated by reference, in their entirety, into the present application.

BACKGROUND OF THE INVENTION

1. Field of the Invention

The present invention relates to an ultrasound transducer that is used for ultrasonography of a subject.

2. Description of the Related Art

Hitherto, ultrasonography in which an examination of a subject is performed by confirming an ultrasound image representing an image of an inside of the subject is known. The ultrasound image is generated by transmitting an ultrasonic beam toward the inside of the subject with an ultrasound transducer including an oscillator array in which a plurality of piezoelectric elements are arranged, receiving an ultrasound echo propagating from the inside of the subject with the ultrasound transducer to obtain an electrical signal, and electrically processing the electrical signal.

In recent years, ultrasonography for supporting treatment of the subject, called Point Of Care (POC), is often performed. In the POC, there is a demand for observation of a fine tissue, such as a muscular structure and a nerve bundle of the subject. From such a demand, for example, as disclosed in JP2016-192666A, to broaden a frequency of an ultrasonic wave for use in forming an ultrasound image to obtain a high-definition ultrasound image, an ultrasound transducer having a plurality of acoustic matching layers has been developed.

SUMMARY OF THE INVENTION

By the way, as disclosed in JP2016-192666A, in a case where a plurality of acoustic matching layers are disposed in the ultrasound transducer, to make an ultrasonic wave be transmitted between the piezoelectric element and the subject, in particular, the acoustic matching layer disposed in the vicinity of the piezoelectric element is required to have high acoustic impedance.

For example, while the acoustic impedance of the acoustic matching layer can be increased by forming the acoustic matching layer of a material having a high acoustic velocity, in a case where the acoustic velocity becomes high, there is a problem in that a resonance frequency due to a width of the acoustic matching layer in an arrangement direction of the piezoelectric elements is close to a resonance frequency in a thickness direction of the piezoelectric element, and image quality of an ultrasound image to be generated is degraded.

The present invention has been accomplished to solve such a problem in the related art, and an object of the present invention is to provide an ultrasound transducer capable of obtaining a high image quality ultrasound image while broadening a frequency of an ultrasonic wave for use in generating an ultrasound image.

To attain the above-described object, there is provided an ultrasound transducer according to the present invention in which a plurality of piezoelectric elements are arranged on a backing material along an arrangement direction, the ultrasound transducer including a plurality of acoustic matching layers laminated on each piezoelectric element, in which at least one acoustic matching layer among the plurality of acoustic matching layers consists of at least one acoustic matching piece having a width narrower than a width of the piezoelectric element in the arrangement direction.

It is preferable that the at least one acoustic matching layer is an acoustic matching layer closest to the piezoelectric element among the plurality of acoustic matching layers.

The plurality of acoustic matching layers may consist of four or more acoustic matching layers of which acoustic impedance decreases in a stepwise manner as a distance from the piezoelectric element increases.

It is preferable that a resonance frequency of the acoustic matching piece in a width direction is higher than a frequency on a high frequency side in a frequency band in which at least a half value of an amplitude value of a resonance frequency of the piezoelectric element in a thickness direction.

It is preferable that the resonance frequency of the acoustic matching piece in the width direction is higher than a frequency on a high frequency side in a frequency band in which a value of 1/10 of the amplitude value of the resonance frequency of the piezoelectric element in the thickness direction is taken.

It is preferable that the at least one acoustic matching layer consists of a plurality of the acoustic matching pieces arranged in the arrangement direction.

The at least one acoustic matching layer may consist of a plurality of the acoustic matching pieces arranged in the arrangement direction and a direction perpendicular to the arrangement direction.

The acoustic matching piece may have any shape of a polygonal column, a circular column, a polygonal cone, or a circular cone extending in a lamination direction of the plurality of acoustic matching layers.

A filler consisting of resin may be disposed between the plurality of the acoustic matching pieces.

According to the present invention, because the ultrasound transducer comprises a plurality of acoustic matching layers laminated on each piezoelectric element, at least one acoustic matching layer among the plurality of acoustic matching layers consists of at least one acoustic matching piece having the width narrower than the width of the piezoelectric element in the arrangement direction, it is possible to obtain a high image quality ultrasound image while broadening a frequency of an ultrasonic wave for use in generating an ultrasound image.

DESCRIPTION OF THE PREFERRED EMBODIMENTS

Hereinafter, an embodiment of the present invention will be described referring to the accompanying drawings.

The description of components described below is provided based on a representative embodiment of the present invention, but the present invention is not limited to such an embodiment.

In the present specification, a numerical range represented using "to" means a range including numerical values before and after "to" as a lower limit value and an upper limit value.

In the present specification, the terms "same" and "identical" include an error range generally allowed in the technical field.

EMBODIMENT

Figure 1:
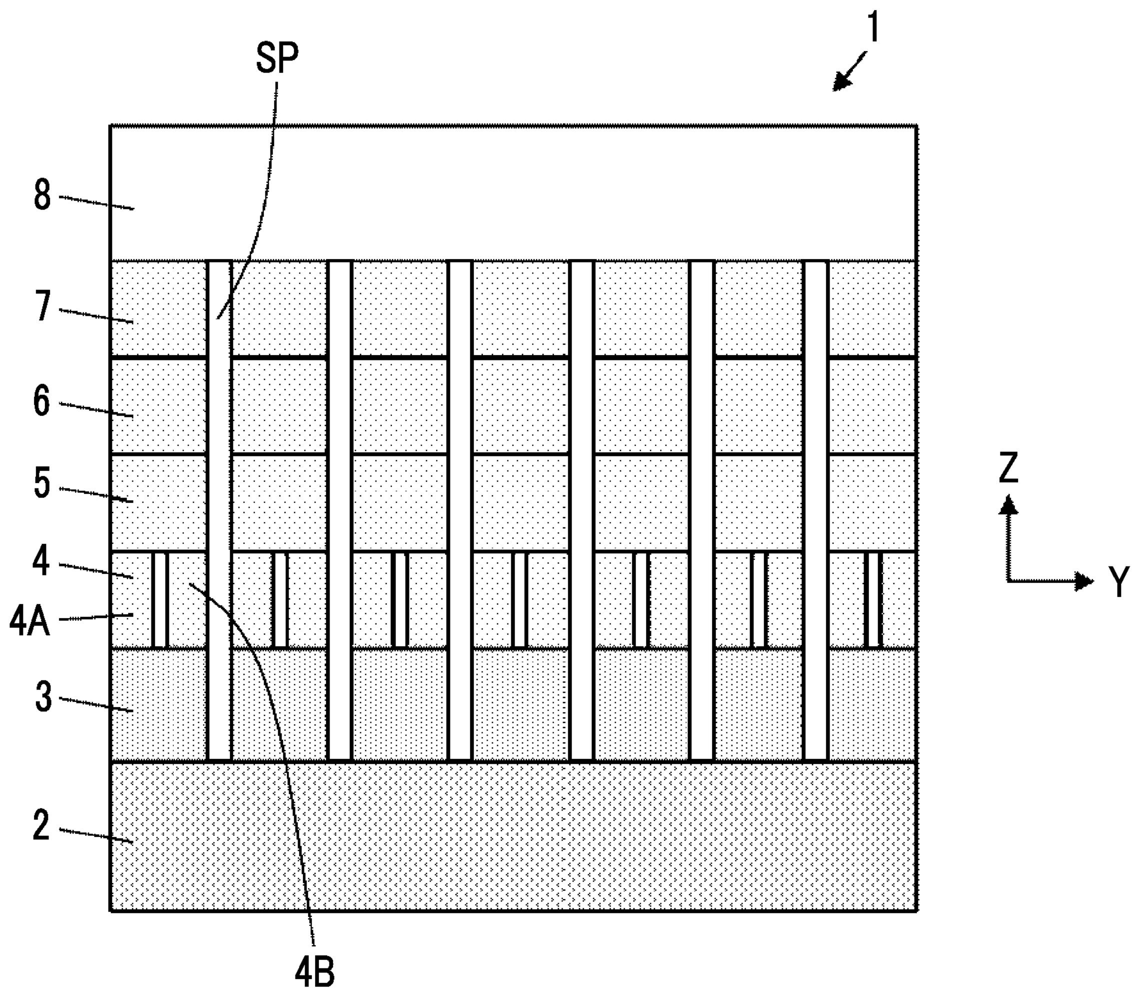
FIG. 1 is a cross-sectional view of an ultrasound transducer according to an embodiment of the present invention.

As shown in FIG. 1, an ultrasound transducer 1 according to the embodiment of the present invention comprises a backing material 2, a plurality of piezoelectric elements 3 that are arranged on the backing material 2 and emits ultrasonic waves, a first acoustic matching layer 4 disposed on each of a plurality of piezoelectric elements 3, a second acoustic matching layer 5 disposed on the first acoustic matching layer 4, a third acoustic matching layer 6 disposed on the second acoustic matching layer 5, a fourth acoustic matching layer 7 disposed on the third acoustic matching layer 6, and an acoustic lens 8 disposed over a plurality of fourth acoustic matching layers 7.

A separating portion that is filled with a filler SP consisting of resin, such as epoxy resin, is formed between adjacent piezoelectric elements 3, adjacent first acoustic matching layers 4, adjacent second acoustic matching layers 5, adjacent third acoustic matching layers 6, and adjacent fourth acoustic matching layers 7.

The first acoustic matching layer 4 has two acoustic matching pieces 4A and 4B having a width narrower than a width of the piezoelectric element 3 in an arrangement direction of the piezoelectric elements 3.

Here, to clarify the invention, the arrangement direction (azimuth direction) of the piezoelectric elements 3 is referred to as a Y direction, a depth direction (elevation direction) of the piezoelectric element 3 is referred to as an X direction, and a lamination direction of the backing material 2, the piezoelectric element 3, the first acoustic matching layer 4, the second acoustic matching layer 5, the third acoustic matching layer 6, the fourth acoustic matching layer 7, and the acoustic lens 8 is referred to as a Z direction.

While lead-out electrodes (not shown) are connected to a plurality of piezoelectric elements 3, respectively, and a flexible print substrate (not shown) connected to a plurality of lead-out electrodes is disposed on a side surface or the like of the backing material 2, the lead-out electrodes and the flexible print substrate are omitted for description.

The piezoelectric element 3 generates an ultrasonic wave in response to a drive signal supplied from a pulser (not shown) or the like connected to the ultrasound transducer 1 and receives an ultrasound echo to output a signal based on the ultrasound echo. The piezoelectric element 3 is configured by forming electrodes at both ends of a piezoelectric body consisting of, for example, piezoelectric ceramic represented by lead zirconate titanate (PZT), a polymer piezoelectric element represented by poly vinylidene di fluoride (PVDF), or piezoelectric single crystal represented by lead magnesium niobate-lead titanate (PMN-PT). The piezoelectric element 3 has a width of about 100 μm to 200 μm in the Y direction.

The backing material 2 supports a plurality of piezoelectric elements 3 and absorbs ultrasonic waves that are emitted from a plurality of piezoelectric elements 3 and propagate backward. The backing material 2 is formed of, for example, a rubber material, such as ferrite rubber.

The acoustic lens 8 is brought into contact with a body surface of a subject at the time of ultrasound diagnosis, converges ultrasonic waves emitted from a plurality of piezoelectric elements 3, and is formed of a resin material, such as epoxy resin, acrylic resin, and polymethyl pentene resin, and a rubber material, such as silicon rubber.

Each of the first acoustic matching layer 4 to the fourth acoustic matching layer 7 matches acoustic impedance between the subject with which the ultrasound transducer 1 is brought into contact and the piezoelectric element 3 in a stepwise manner, and facilitates incidence of the ultrasonic wave into the subject. The first acoustic matching layer 4 to the fourth acoustic matching layer 7 are composed of, for example, a resin material, such as epoxy resin or urethane resin.

Figure 2:
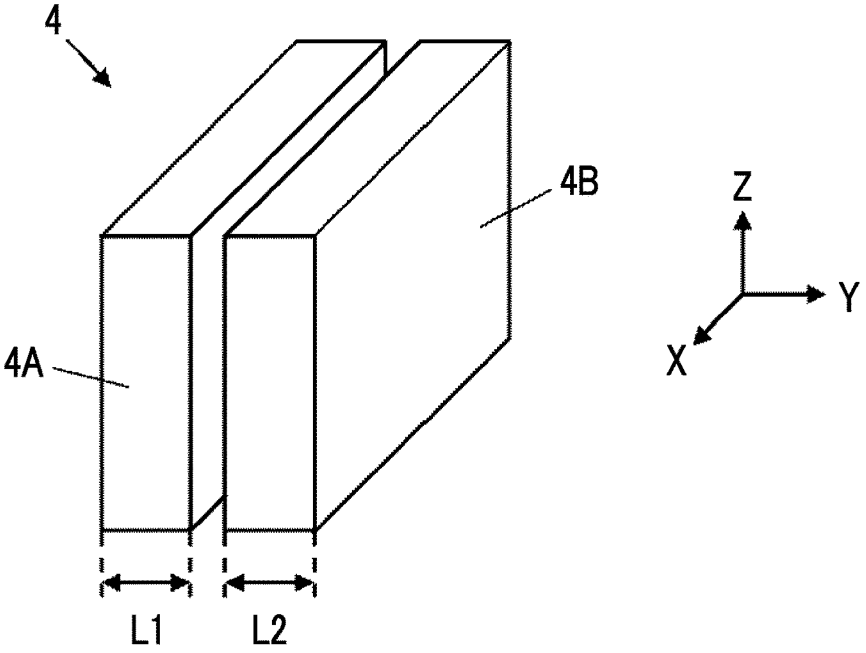
FIG. 2 is a perspective view of a first acoustic matching layer in the embodiment of the present invention.

As shown in FIG. 2, the acoustic matching pieces 4A and 4B of the first acoustic matching layer 4 have a plate shape parallel to an XZ plane and are disposed to be adjacent to each other and to be spaced from each other in the Y direction. The acoustic matching piece 4A has a width L1 in the Y direction, and the acoustic matching piece 4B has a width L2 in the Y direction. Each of the width L1 of the acoustic matching piece 4A and the width L2 of the acoustic matching piece 4B is narrower than a width of the piezoelectric element 3 in the Y direction.

The acoustic matching pieces 4A and 4B of the first acoustic matching layer 4 are composed of a material having acoustic impedance higher than the material composing the second acoustic matching layer 5, the material composing the third acoustic matching layer 6, and the material composing the fourth acoustic matching layer 7, and having acoustic impedance lower than the piezoelectric element 3.

Here, in general, while it is known that acoustic impedance of a medium is represented by a product of density of the medium and an acoustic velocity in the medium, a material having comparatively high acoustic impedance indicates a material having a comparatively high acoustic velocity, and a material having comparatively low acoustic impedance indicates a material having a comparatively low acoustic velocity.

The second acoustic matching layer 5 is composed of a material having acoustic impedance higher than the material composing the third acoustic matching layer 6 and the material composing the fourth acoustic matching layer 7 and having acoustic impedance lower than the material composing the acoustic matching pieces 4A and 4B of the first acoustic matching layer 4.

The third acoustic matching layer 6 is composed of a material having acoustic impedance higher than the material composing the fourth acoustic matching layer 7 and having acoustic impedance lower than the material composing the second acoustic matching layer 5.

The fourth acoustic matching layer 7 is composed of a material having acoustic impedance higher than the acoustic impedance of the subject and having acoustic impedance lower than the material composing the third acoustic matching layer 6.

In this way, acoustic impedance decreases in a stepwise manner in an order of the piezoelectric element 3, the first acoustic matching layer 4, the second acoustic matching layer 5, the third acoustic matching layer 6, and the fourth acoustic matching layer 7, that is, the first acoustic matching layer 4 to the fourth acoustic matching layer 7 are designed such that the acoustic impedance decreases in a stepwise manner as a distance from the piezoelectric element 3 increases.

The ultrasound transducer 1 of the embodiment is used to generate an ultrasound image by transmitting the ultrasonic waves generated from a plurality of piezoelectric elements 3 with a drive voltage from the pulser (not shown) or the like into the subject in a state in which the acoustic lens 8 is brought into contact with the body surface of the subject, converting ultrasound echoes reflected by a tissue or the like in the subject into electrical signals in a plurality of piezoelectric elements 3, and electrically processing the obtained electrical signals using an external apparatus.

The ultrasonic wave generated by the piezoelectric element 3 is transmitted into the subject through the first acoustic matching layer 4, the second acoustic matching layer 5, the third acoustic matching layer 6, the fourth acoustic matching layer 7, and the acoustic lens 8. The ultrasound echo that propagates from the inside of the subject toward the ultrasound transducer 1 is incident on the piezoelectric element 3 through the acoustic lens 8, the fourth acoustic matching layer 7, the third acoustic matching layer 6, the second acoustic matching layer 5, and the first acoustic matching layer 4, and the incident ultrasound echo is converted into the electrical signal in the piezoelectric element 3.

In the ultrasound transducer 1, because the four acoustic matching layers of the first acoustic matching layer 4 to the fourth acoustic matching layer 7 are disposed such that acoustic impedance gradually decreases from the piezoelectric element 3 side toward the acoustic lens 8 side, for example, even though a frequency of the ultrasonic wave emitted from the piezoelectric element 3 becomes sufficiently high, the ultrasonic wave is easily transmitted between the piezoelectric element 3 and the acoustic lens 8, and the frequency of the ultrasonic wave for use in forming the ultrasound image can be broadened.

Figure 3:
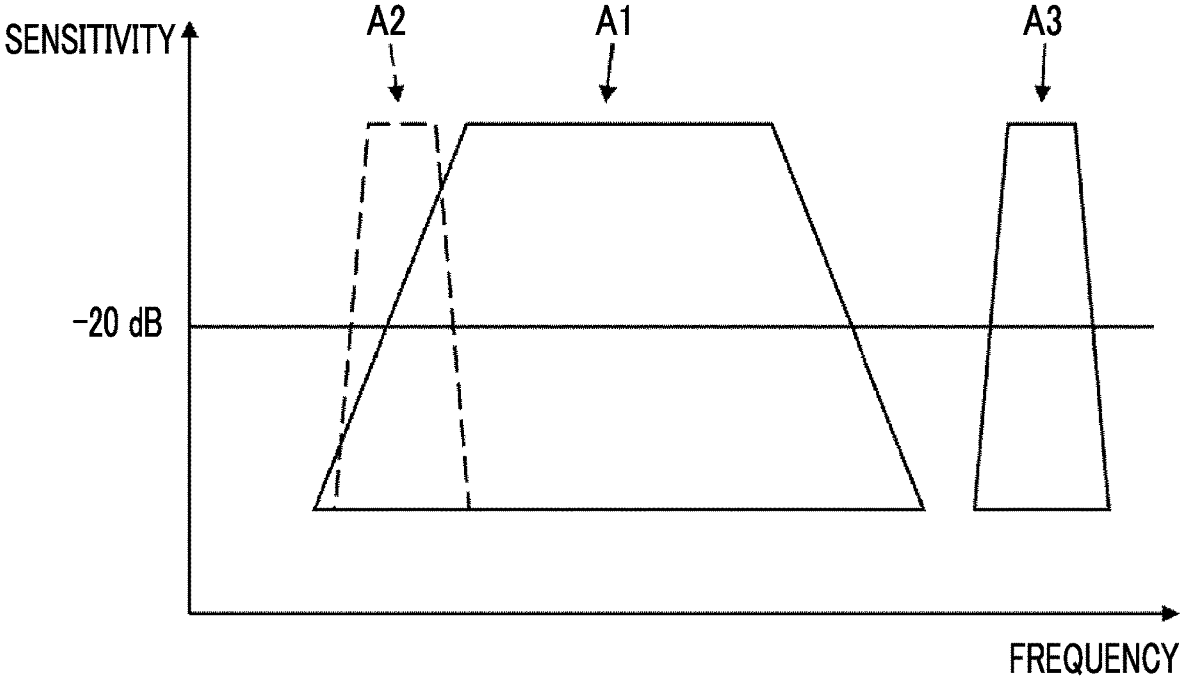
FIG. 3 is a diagram schematically representing a frequency band of a piezoelectric element and a frequency band including a resonance frequency due to a width of an acoustic matching piece of the first acoustic matching layer in the embodiment of the present invention.

Here, a frequency band of the ultrasonic wave for use in generating the ultrasound image includes a resonance frequency due to a thickness of the piezoelectric element 3 in the Z direction, and changes like a frequency band A1 depending on sensitivity as schematically shown in FIG. 3, for example.

Normally, in a case where a plurality of acoustic matching layers are disposed to broaden the frequency band A1, to match acoustic impedance between the subject with which the ultrasound transducer 1 is brought into contact and the piezoelectric element 3, in particular, the acoustic matching layer disposed in the vicinity of the piezoelectric element 3 needs to be composed of a material having high acoustic impedance. Assuming that the acoustic matching layer composed of the material having high acoustic impedance has one acoustic matching piece, and the width of the acoustic matching layer in the Y direction is substantially the same as the width of the piezoelectric element 3 in the Y direction, as shown in FIG. 3, a frequency band A2 including a resonance frequency due to the width of the acoustic matching layer in the Y direction may overlap the frequency band A1 of the piezoelectric element 3.

In a case of generating a high-definition ultrasound image to observe a fine tissue, such as a muscular structure and a nerve bundle of the subject, for example, sensitivity of −20 dB is often used; however, in a case where the frequency band A1 of the piezoelectric element 3 at the sensitivity overlaps the frequency band A2 due to the width of the acoustic matching layer in the Y direction, image quality of the ultrasound image to be generated is deteriorated due to the frequency band A2.

Because the acoustic matching piece 4A in the present embodiment has the width L1 narrower than the width of the piezoelectric element 3 in the Y direction, a resonance frequency due to the width L1 of the acoustic matching piece 4A is higher than a resonance frequency in a case of assuming that the acoustic matching piece 4A has the same width as the width of the piezoelectric element 3 in the Y direction. For this reason, the resonance frequency due to the width L1 of the acoustic matching piece 4A is made higher than a frequency on a high frequency side in the frequency band A1 of the piezoelectric element 3 at the sensitivity for use in generating a high-definition ultrasound image, such as −20 Db, by adjusting the width L1 of the acoustic matching piece 4A, whereby a frequency band A3 that does not overlap the frequency band A1 can be obtained.

The acoustic matching piece 4B disposed to be adjacent to the acoustic matching piece 4A in the Y direction has the width L2 narrower than the width of the piezoelectric element 3 in the Y direction, and a resonance frequency due to the width L2 of the acoustic matching piece 4B is higher than a resonance frequency in a case of assuming that the acoustic matching piece 4B has the same width as the width of the piezoelectric element 3 in the Y direction. For this reason, the resonance frequency due to the width L2 of the acoustic matching piece 4B is made higher than a frequency on a high frequency side in the frequency band A1 of the piezoelectric element 3 at the sensitivity for use in generating a high-definition ultrasound image, such as 20 dB, by adjusting the width L2 of the acoustic matching piece 4B similarly to the acoustic matching piece 4A, whereby a frequency band that does not overlap the frequency band A1 can be obtained.

In this way, because the first acoustic matching layer 4 has the acoustic matching piece 4A having the width L1 narrower than the width of the piezoelectric element 3 in the Y direction and the acoustic matching piece 4B having the width L2 narrower than the width of the piezoelectric element 3 in the Y direction, even though the acoustic matching pieces 4A and 4B are composed of a material having sufficiently high acoustic impedance, at the sensitivity for use in generating an ultrasound image, the frequency band A1 of the piezoelectric element 3 and the frequency band A3 due to the width L1 of the acoustic matching piece 4A can be separated from each other, and the frequency band A1 of the piezoelectric element 3 and the frequency band due to the width L2 of the acoustic matching piece 4B can be separated from each other.

From the above, with the ultrasound transducer 1 of the embodiment, because a plurality of acoustic matching layers of the first acoustic matching layer 4 to the fourth acoustic matching layer 7 are provided, and the first acoustic matching layer 4 has the acoustic matching piece 4A having the width L1 narrower than the width of the piezoelectric element 3 in the Y direction and the acoustic matching piece 4B having the width L2 narrower than the width of the piezoelectric element 3 in the Y direction, it is possible to obtain a high image quality ultrasound image while broadening the frequency band A1 for use in generating an ultrasound image.

Figure 4:
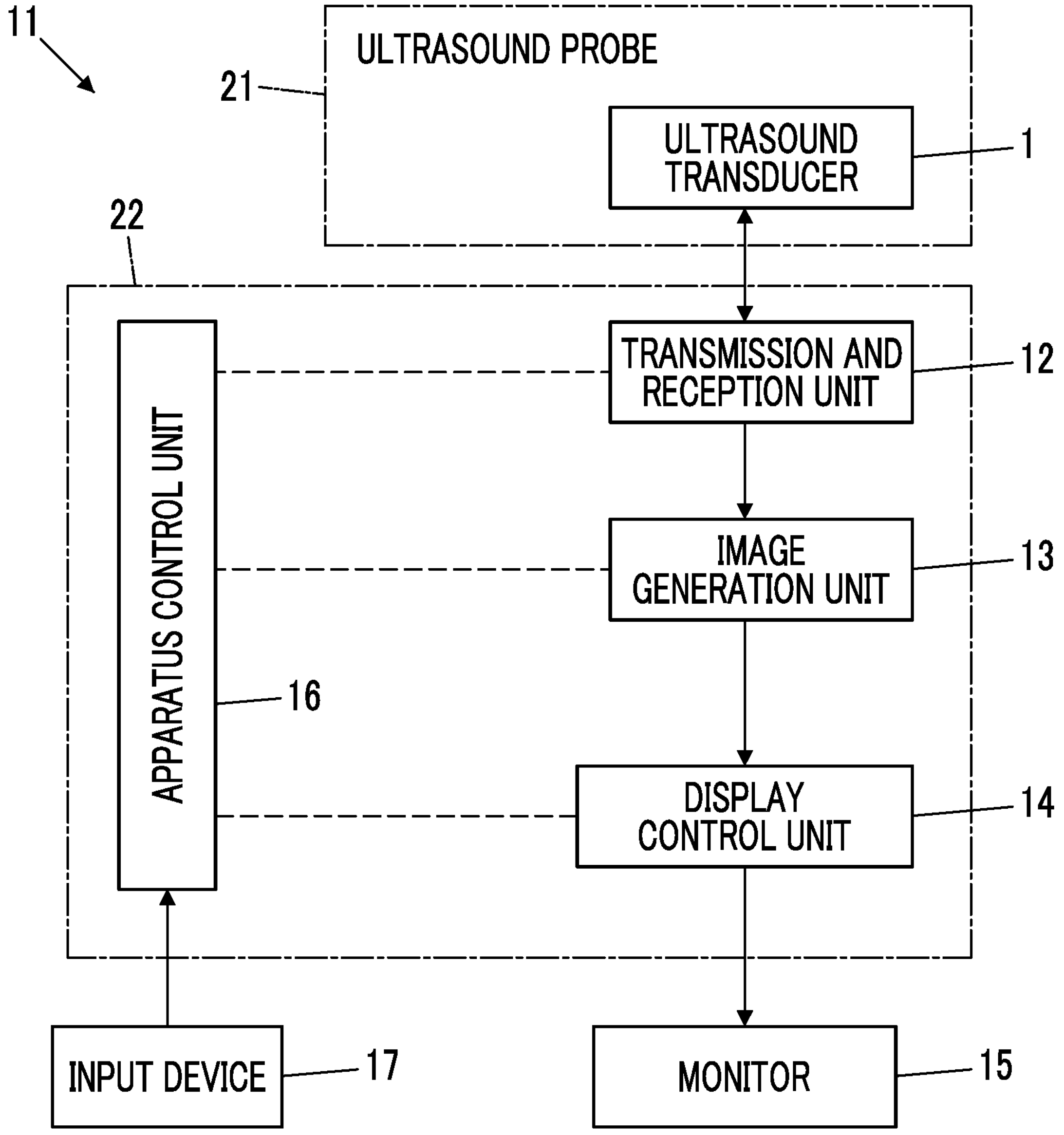
FIG. 4 is a block diagram showing a configuration of an ultrasound diagnostic apparatus having the ultrasound transducer in the embodiment of the present invention.

Next, an ultrasound diagnostic apparatus 11 having the ultrasound transducer 1 according to the embodiment of the present invention will be described. As shown in FIG. 4, in the ultrasound diagnostic apparatus 11, a transmission and reception unit 12, an image generation unit 13, a display control unit 14, and a monitor 15 are sequentially connected to the ultrasound transducer 1. An apparatus control unit 16 is connected to the transmission and reception unit 12, the image generation unit 13, and the display control unit 14. An input device 17 is connected to the apparatus control unit 16. A memory (not shown) is connected to the apparatus control unit 16.

Furthermore, the ultrasound diagnostic apparatus 11 comprises an ultrasound probe 21 including the ultrasound transducer 1. A processor 22 for the ultrasound diagnostic apparatus 11 is configured with the transmission and reception unit 12, the image generation unit 13, the display control unit 14, and the apparatus control unit 16.

Figure 5:
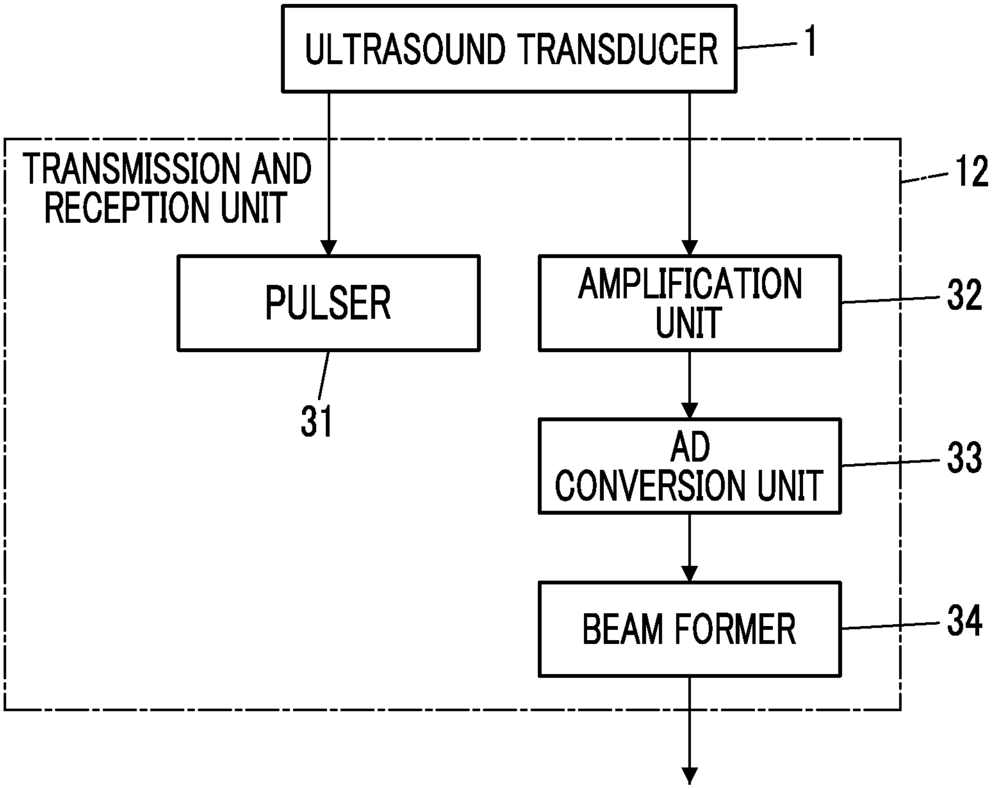
FIG. 5 is a block diagram showing an internal configuration of a transmission and reception unit in the embodiment of the present invention.

The transmission and reception unit 12 transmits the ultrasonic waves from the ultrasound transducer 1 and generates sound ray signals based on reception signals acquired by the ultrasound transducer 1 under the control of the apparatus control unit 16. As shown in FIG. 5, the transmission and reception unit 12 has a pulser 31 that is connected to the ultrasound transducer 1, and an amplification unit 32, an analog digital (AD) conversion unit 33, and a beam former 34 that are sequentially connected in series from the ultrasound transducer 1.

The pulser 31 includes, for example, a plurality of pulse generators, adjusts a delay amount of each of drive signals based on a transmission delay pattern selected in response to a control signal from the apparatus control unit 16 such that the ultrasonic waves transmitted from a plurality of piezoelectric elements 3 of the ultrasound transducer 1 form an ultrasonic beam, and supplies the drive signals to a plurality of piezoelectric elements 3. In this way, in a case where a pulsed or continuous-wave voltage is applied to the electrodes of the piezoelectric elements 3, the piezoelectric elements 3 expand and contract, a pulsed or continuous-wave ultrasonic wave is generated from each of the piezoelectric elements 3, and an ultrasonic beam is formed from a combined wave of the ultrasonic waves.

The transmitted ultrasonic beam is reflected by, for example, a tissue in the subject and propagates toward the ultrasound transducer 1 of the ultrasound probe 21. Each of the piezoelectric elements 3 of the ultrasound transducer 1 expands and contracts with reception of the ultrasound echo propagating toward the ultrasound transducer 1 in this manner, generates a reception signal that is an electrical signal, and outputs the reception signal to the amplification unit 32.

The amplification unit 32 amplifies the signal input from each of the piezoelectric elements 3 of the ultrasound transducer 1 and transmits the amplified signal to the AD conversion unit 33. The AD conversion unit 33 converts the signal transmitted from the amplification unit 32 into digital reception data and transmits the reception data to the beam former 34. The beam former 34 performs so-called reception focus processing by giving a delay to each piece of reception data converted into digital data by the AD conversion unit 33 conforming to an acoustic velocity or a distribution of an acoustic velocity set based on a reception delay pattern selected in response to a control signal from the apparatus control unit 16 and performing addition. With the reception focus processing, a sound ray signal obtained by performing phasing addition on each piece of reception data converted with the AD conversion unit 33 and narrowing down a focus of the ultrasound echo is acquired.

Figure 6:
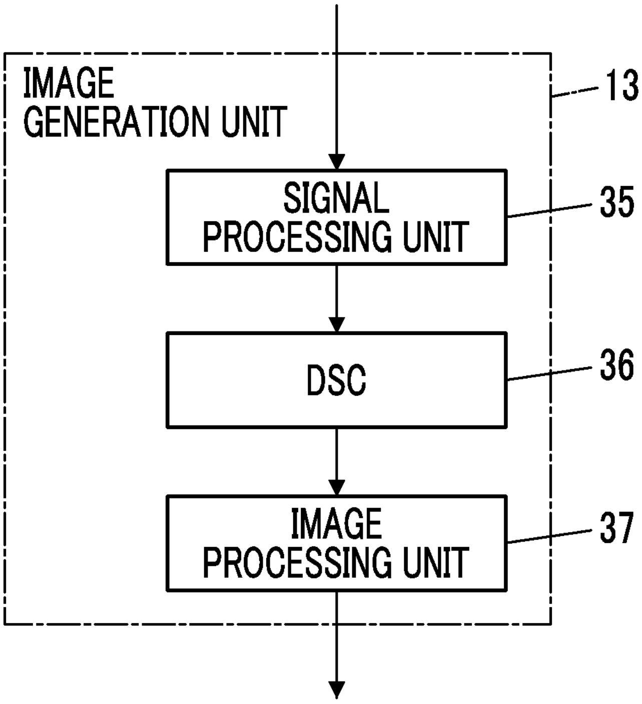
FIG. 6 is a block diagram showing an internal configuration of an image generation unit in the embodiment of the present invention.

As shown in FIG. 6, the image generation unit 13 has a configuration in which a signal processing unit 35, a digital scan converter (DSC) 36, and an image processing unit 37 are sequentially connected in series.

The signal processing unit 35 performs correction of attenuation on the sound ray signal generated by the beam former 34 of the transmission and reception unit 12 due to a distance depending on a depth of a reflection position of an ultrasonic wave, and then, executes envelope detection processing, thereby generating a B mode image signal that is tomographic image information regarding the tissue in the subject.

The DSC 36 converts (raster-converts) the B mode image signal generated in the signal processing unit 35 into an image signal conforming to a normal television signal scanning method.

The image processing unit 37 executes various kinds of necessary image processing, such as gradation processing, on the B mode image signal input from the DSC 36, and then, outputs the B mode image signal to the display control unit 14. In the present invention, the B mode image signal subjected to the image processing by the image processing unit 37 is simply referred to as an ultrasound image.

The display control unit 14 executes predetermined processing on the ultrasound image generated by the image generation unit 13 and displays the ultrasound image on the monitor 15 under the control of the apparatus control unit 16.

The monitor 15 displays the ultrasound image generated by the image generation unit 13 under the control of the display control unit 14, and includes, for example, a display device, such as a liquid crystal display (LCD) or an organic electroluminescence display (organic EL display).

The apparatus control unit 16 performs control of each unit of the ultrasound diagnostic apparatus 11 based on a control program or the like stored in advance.

The input device 17 is provided for the user to perform an input operation, and can comprise a keyboard, a mouse, a trackball, a touch pad, a touch panel, and the like.

Though not shown, a memory that is connected to the apparatus control unit 16 stores the control program of the ultrasound diagnostic apparatus 11, and the like, and as the memory, a recording medium, such as a flash memory, a hard disc drive (HDD), a solid state drive (SSD), a flexible disc (FD), a magneto-optical disc (MO disc)), a magnetic tape (MT), a random access memory (RAM), a compact disc (CD), a digital versatile disc (DVD), a secure digital card (SD card), or a universal serial bus memory (USB memory), a server, or the like can be used.

Although the processor 22 having the transmission and reception unit 12, the image generation unit 13, the display control unit 14, and the apparatus control unit 16 is configured with a central processing unit (CPU) and a control program causing the CPU to execute various kinds of processing, the processor 22 may be configured using a field programmable gate array (FPGA), a digital signal processor (DSP), an application specific integrated circuit (ASIC), a graphics processing unit (GPU), and other integrated circuits (ICs) or may be configured by combining such ICs.

The transmission and reception unit 12, the image generation unit 13, the display control unit 14, and the apparatus control unit 16 of the processor 22 may be configured to be partially or wholly integrated into one CPU or the like.

Because the ultrasound diagnostic apparatus 11 in the embodiment of the present invention comprises the ultrasound transducer 1 according to the embodiment of the present invention, it is possible to obtain a high image quality ultrasound image while broadening a frequency band of an ultrasonic wave transmitted from the ultrasound transducer 1 to the subject by the transmission and reception unit 12 and a frequency band of an ultrasonic wave received in the ultrasound transducer 1.

As shown in FIG. 1, as the filler SP that is filled between adjacent piezoelectric elements 3, adjacent first acoustic matching layers 4, adjacent second acoustic matching layers 5, adjacent third acoustic matching layers 6, and adjacent fourth acoustic matching layers 7, for example, silicon resin, such as RTV630 manufactured by Momentive Performance Materials Inc., epoxy resin, such as EpoteK 310M manufactured by Epoxy Technology Inc., and urethane resin can be used.

A filler similar to the filler SP can be filled between the acoustic matching piece 4A and the acoustic matching piece 4B disposed to be adjacent to each other in the first acoustic matching layer 4. With this, the acoustic matching piece 4A and the acoustic matching piece 4B are prevented from being in contact with each other due to any cause, and the acoustic matching pieces 4A and 4B can be disposed more stably.

Although the materials composing the first acoustic matching layer 4 to the fourth acoustic matching layer 7 are not particularly limited, for example, a material obtained by kneading fine particles of metal, fine particles of metal oxide, or fine particles of ceramic with a resin material, such as epoxy resin or urethane resin, in a vacuum defoaming mixer or a planetary mixer, such as AWATORI RENTARO ARV-310P manufactured by THINKY CORPORATION. In this case, adjustment of the total number of fine particles that are kneaded with the resin material allows an acoustic velocity in the completed material to be adjusted.

As a material of the fine particles, for example, iron, tungsten, alumina, zirconia, or silica can be used. The fine particles preferably have a diameter equal to or greater than 0.01 and equal to or smaller than 100.00 μm and more preferably have a diameter equal to or greater than 0.10 μm and equal to or smaller than 10.00 μm to reduce attenuation of an ultrasonic wave in the first acoustic matching layer 4 to the fourth acoustic matching layer 7.

Although a case where the resonance frequency of the acoustic matching piece 4A in the width direction, that is, the resonance frequency due to the width L1 is higher than the frequency on the high frequency side of the frequency band A1 of the piezoelectric element 3 at the sensitivity of −20 dB, for example, to obtain a high-definition ultrasound image has been described, in a case where the resonance frequency of the acoustic matching piece 4A in the width direction is higher than a frequency on a high frequency side in a frequency band in which at least a half value of an amplitude value of a resonance frequency of the piezoelectric element 3 in a thickness direction is taken, it is possible to obtain a high-definition ultrasound image without causing degradation of image quality. From a viewpoint of obtaining a high-definition ultrasound image without causing degradation of image quality, it is more preferable that the resonance frequency due to the width L1 of the acoustic matching piece 4A is higher than a frequency on a high frequency side in a frequency band in which a value of 1/10 of amplitude value of the resonance frequency of the piezoelectric element 3 in the thickness direction is taken.

Similarly to the resonance frequency due to the width L1 of the acoustic matching piece 4A, the resonance frequency due to the width L2 of the acoustic matching piece 4B is preferably higher than the frequency on the high frequency side in the frequency band in which at least the half value of the amplitude value of the resonance frequency of the piezoelectric element 3 in the thickness direction is taken, and is more preferably higher than the frequency on the high frequency side in the frequency band in which the value of 1/10 of amplitude value of the resonance frequency of the piezoelectric element 3 in the thickness direction is taken.

Also at sensitivity for use in a case of generating a normal ultrasound image, such as −6 dB, not in a case of generating a high-definition ultrasound image, to obtain a high image quality ultrasound image, the resonance frequency due to the width L1 of the acoustic matching piece 4A and the resonance frequency due to the width L2 of the acoustic matching piece 4B are preferably higher than the frequency on the high frequency side in the frequency band A1 of the piezoelectric element 3 in the thickness direction.

The width L1 of the acoustic matching piece 4A and the width L2 of the acoustic matching piece 4B of the first acoustic matching layer 4 can have the same length or can have different lengths. Also in this case, because the width L1 of the acoustic matching piece 4A and the width L2 of the acoustic matching piece 4B are narrower than the width of the piezoelectric element 3 in the Y direction, the resonance frequency due to the width L1 of the acoustic matching piece 4A and the resonance frequency due to the width L2 of the acoustic matching piece 4B can be made to be higher than the frequency on the high frequency side of the frequency band A1 of the piezoelectric element 3.

Although a case where the first acoustic matching layer 4 has the two acoustic matching pieces 4A and 4B has been described, the first acoustic matching layer 4 can have three or more acoustic matching pieces disposed in parallel in the Y direction. In a case where the first acoustic matching layer 4 has three or more acoustic matching pieces, because the width of each acoustic matching piece in the Y direction can be narrowed compared to a case where the first acoustic matching layer 4 has the two acoustic matching pieces 4A and 4B, a resonance frequency due to the width of each acoustic matching piece in the Y direction can be made to be even higher than the frequency on the high frequency side of the frequency band A1 of the piezoelectric element 3.

Figure 7:
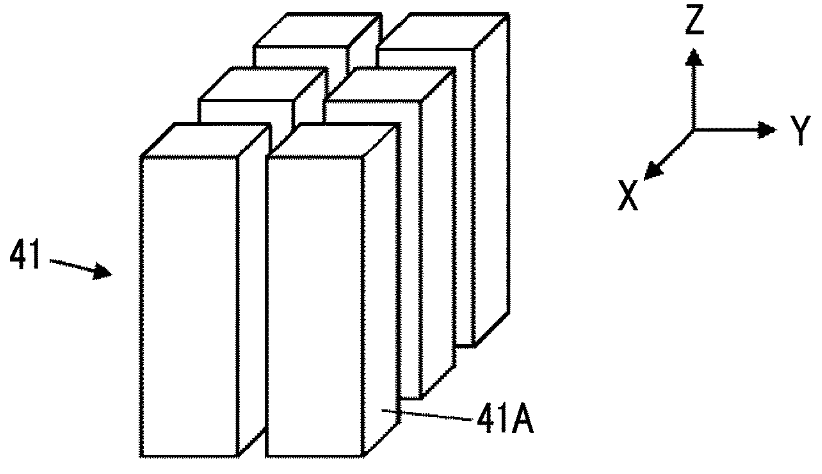
FIG. 7 is a perspective view of a first acoustic matching layer in a first modification example of the embodiment of the present invention.

The first acoustic matching layer 4 may have a plurality of acoustic matching pieces arranged in each of the Y direction and the X direction, for example, as shown in FIG. 7. In an example of FIG. 7, the first acoustic matching layer 41 has a plurality of acoustic matching pieces 41A having a quadrangular columnar shape. A plurality of acoustic matching pieces 41A are disposed through a gap in each of the X direction and the Y direction.

The gap between a plurality of acoustic matching pieces 41A can be filled with a filler similar to the filler SP.

Figure 8:
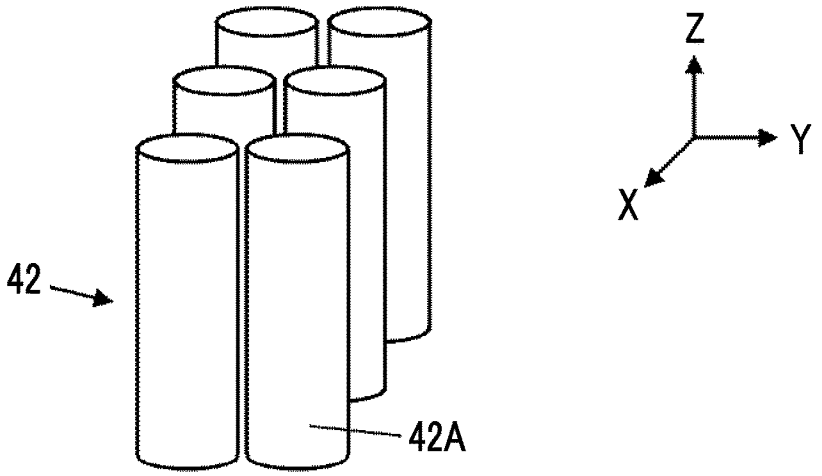
FIG. 8 is a perspective view of a first acoustic matching layer in a second modification example of the embodiment of the present invention.

For example, as shown in FIG. 8, the first acoustic matching layer 42 can have a plurality of acoustic matching pieces 42A having a circular columnar shape.

In FIGS. 7 and 8, although the quadrangular columnar shape and the circular columnar shape are illustrated as the shape of the acoustic matching pieces 41A and 42A, acoustic matching pieces having any columnar shape, such as a regular polygonal column, may be used, or acoustic matching pieces having any conic shape, such as a circular cone, may be used. The acoustic matching piece having such a shape can be formed by, for example, a technique, such as etching.

The number of acoustic matching pieces configuring each of the first acoustic matching layers 4, 41, and 42 is not particularly limited as long as the width of the acoustic matching piece in the Y direction is narrower than the width of the piezoelectric element 3 in the Y direction.

Figure 9:
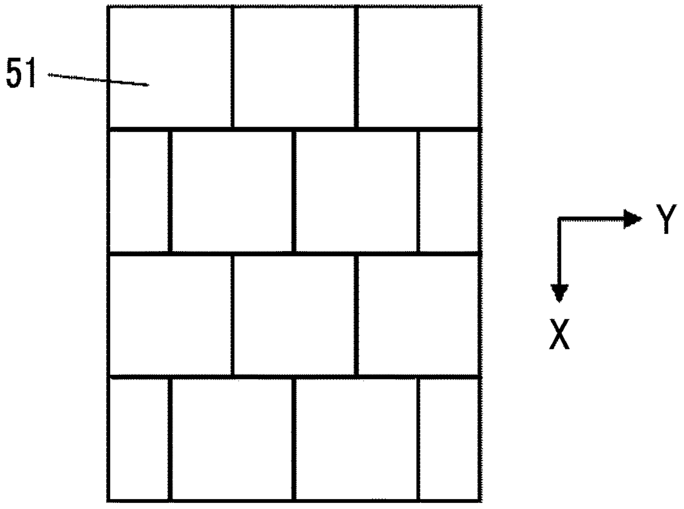
FIG. 9 is a top view of a first acoustic matching layer in a third modification example of the embodiment of the present invention.
Figure 10:
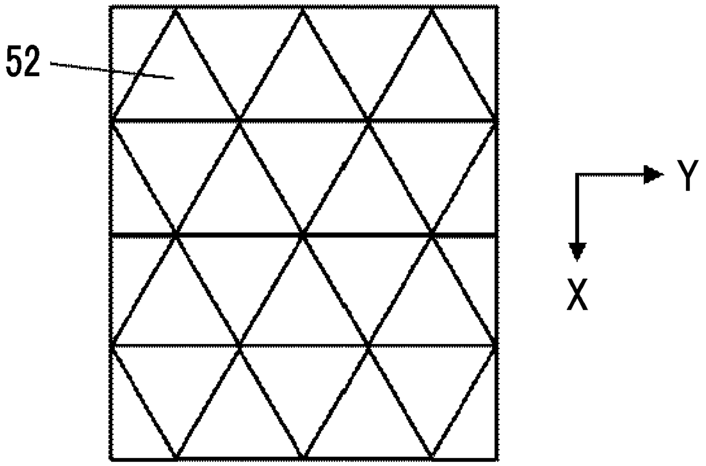
FIG. 10 is a top view of a fourth acoustic matching layer in a second modification example of the embodiment of the present invention.
Figure 11:
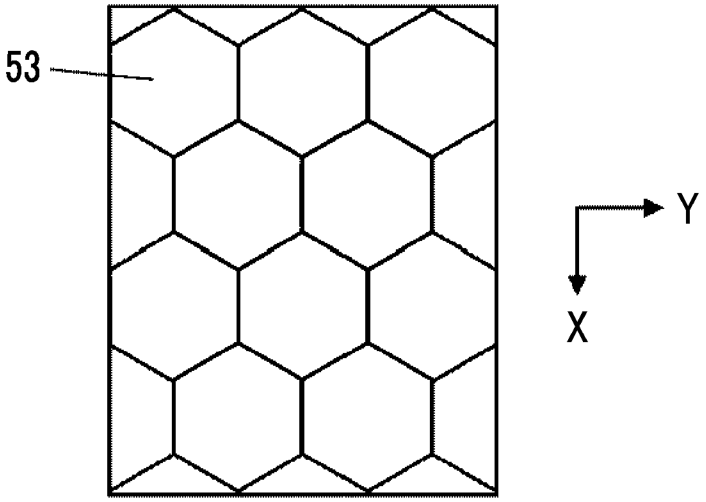
FIG. 11 is a top view of a fifth acoustic matching layer in a second modification example of the embodiment of the present invention.

A plurality of acoustic matching pieces of each of the first acoustic matching layers 4, 41, and 42 may be arranged to have, for example, a pattern shown in FIGS. 9 to 11 as viewed from a +Z direction. In an example shown in FIG. 9, a plurality of quadrangular columnar acoustic matching pieces 51 are disposed to be alternately shifted in the X direction. In an example shown in FIG. 10, a plurality of regular triangular columnar acoustic matching pieces 52 are arranged to be most densely filled within an XY plane. In an example shown in FIG. 11, a plurality of regular hexagonal columnar acoustic matching pieces 53 are arranged to be most densely filled within the XY plane, and a so-called honeycomb pattern is formed.

For each first acoustic matching layer 4, 41, or 42 among a plurality of first acoustic matching layers 4, 41, or 42 arranged in the Y direction of the ultrasound transducer 1, it can be designed such that a total value of widths of a plurality of acoustic matching pieces in the Y direction is changed. With this, it is possible to locally adjust an acoustic velocity of ultrasonic waves emitted from the ultrasound transducer 1, in the Y direction. With this, it is possible to perform acoustic design of the ultrasound transducer 1 in various ways.

In a case of the first acoustic matching layers 4, 41, and 42 positioned in a central portion of the ultrasound transducer 1 in the X direction, a plurality of acoustic matching pieces can be comparatively densely disposed in the X direction, and in a case where the first acoustic matching layers 4, 41, and 42 positioned in both end portions of the ultrasound transducer 1 in the X direction, a plurality of acoustic matching pieces can be comparatively sparsely disposed in the X direction. With this, like a technique of so-called apodization, it is possible to suppress discharge of an ultrasonic beam emitted from both end portions of the ultrasound transducer 1 in the X direction to reduce so-called side lobe that the ultrasonic beam is narrowed and the ultrasonic beam is discharged in a direction out of the central portion of the ultrasound transducer 1 in the X direction.

Although a case where only the first acoustic matching layer 4 among the first acoustic matching layer 4 to the fourth acoustic matching layer 7 has a plurality of acoustic matching pieces has been described, at least one of the first acoustic matching layer 4 to the fourth acoustic matching layer 7 may have a plurality of acoustic matching pieces. Note that, because the first acoustic matching layer 4 positioned in the most vicinity of the piezoelectric element 3 is composed of a material having acoustic impedance higher than the second acoustic matching layer 5 to the fourth acoustic matching layer 7, from a viewpoint of obtaining a high image quality ultrasound image, it is most preferable that the first acoustic matching layer 4 has a plurality of acoustic matching pieces.

Although a case where the ultrasound transducer 1 has the four acoustic matching layers of the first acoustic matching layer 4 to the fourth acoustic matching layer 7 has been described, the ultrasound transducer 1 can have five or more acoustic matching layers. As the ultrasound transducer 1 has more acoustic matching layers, the acoustic matching layer disposed at a position close to the piezoelectric element 3 needs to be composed of a material having high acoustic impedance. Thus, in a case where the acoustic matching layer has one acoustic matching piece, it is considered that the resonance frequency due to the width of the acoustic matching piece in the Y direction is easily close to the frequency band A1 of the piezoelectric element 3. In the ultrasound transducer 1 of the present invention, the width of the acoustic matching piece in the Y direction is narrower than the width of the piezoelectric element 3 in the Y direction, so that the frequency band A1 of the piezoelectric element 3 and the frequency band due to the width of the acoustic matching piece in the Y direction can be separated from each other. Thus, it is useful as the ultrasound transducer 1 has more acoustic matching layers.

Although a case where the transmission and reception unit 12 is included in the processor 22 has been described, the transmission and reception unit 12 can be configured with an electric circuit.

Alternatively, the transmission and reception unit 12 may be included in the ultrasound probe 21.

In this way, even in a case where the transmission and reception unit 12 is configured with an electric circuit and even in a case where the transmission and reception unit 12 is included in the ultrasound probe 21, because the ultrasound diagnostic apparatus 11 in the embodiment of the present invention comprises the ultrasound transducer 1 according to the embodiment of the present invention, it is possible to obtain a high image quality ultrasound image while broadening the frequency band of the ultrasonic wave transmitted from the ultrasound transducer 1 to the subject with the transmission and reception unit 12 and the frequency band of the ultrasonic wave received in the ultrasound transducer 1.

EXPLANATION OF REFERENCES

1: ultrasound transducer
2: backing material
3: piezoelectric element
4, 41, 42: first acoustic matching layer
4A, 4B, 41A, 42A, 51, 52, 53: acoustic matching piece
5: second acoustic matching layer
6: third acoustic matching layer
7: fourth acoustic matching layer
8: acoustic lens
11: ultrasound diagnostic apparatus
12: transmission and reception unit
13: image generation unit
14: display control unit
15: monitor
16: apparatus control unit
17: input device
21: ultrasound probe
22: processor

31: pulser
32: amplification unit
33: AD conversion unit
34: beam former
signal processing unit
36: DSC
37: image processing unit
A1, A2, A3: frequency band
L1, L2: width
SP: filler.

What is claimed is:

1. An ultrasound transducer in which a plurality of piezoelectric elements are arranged on a backing material along an arrangement direction, the ultrasound transducer comprising:

a plurality of acoustic matching layers laminated on each of the plurality of piezoelectric elements in a thickness direction of the plurality of piezoelectric elements, the thickness direction crossing the arrangement direction, wherein one acoustic matching layer among the plurality of acoustic matching layers laminated on any one piezoelectric element of the plurality of piezoelectric elements comprises at least two acoustic matching pieces with at least one gap located therebetween, wherein each acoustic matching piece has a width narrower than a width of the any one piezoelectric element in the arrangement direction, the at least two acoustic matching pieces and the at least one gap being arranged in the arrangement direction, and the at least one gap is filled by a filler consisting of resin.

2. The ultrasound transducer according to claim 1, wherein the at least one acoustic matching layer is an acoustic matching layer closest to the piezoelectric element among the plurality of acoustic matching layers.

3. The ultrasound transducer according to claim 2, wherein the plurality of acoustic matching layers consist of four or more acoustic matching layers of which acoustic impedance decreases in a stepwise manner as a distance from the piezoelectric element increases.

4. The ultrasound transducer according to claim 2, wherein a resonance frequency of each of the plurality of acoustic matching pieces in a width direction is higher than a frequency on a high frequency side in a frequency band in which at least a half value of an amplitude value of a resonance frequency of the piezoelectric element in a thickness direction is taken.

5. The ultrasound transducer according to claim 1, wherein the plurality of acoustic matching layers consist of four or more acoustic matching layers of which acoustic impedance decreases in a stepwise manner as a distance from the piezoelectric element increases.

6. The ultrasound transducer according to claim 5, wherein a resonance frequency of each of the plurality of acoustic matching pieces in a width direction is higher than a frequency on a high frequency side in a frequency band in which at least a half value of an amplitude value of a resonance frequency of the piezoelectric element in a thickness direction is taken.

7. The ultrasound transducer according to claim 1, wherein a resonance frequency of each of the plurality of acoustic matching pieces in a width direction is higher than a frequency on a high frequency side in a frequency band in which at least a half value of an amplitude value of a resonance frequency of the piezoelectric element in a thickness direction is taken.

8. The ultrasound transducer according to claim 7, wherein the resonance frequency of each of the plurality of acoustic matching pieces in the width direction is higher than a frequency on a high frequency side in a frequency band in which a value of 1/10 of the amplitude value of the resonance frequency of the piezoelectric element in the thickness direction is taken.

9. The ultrasound transducer according to claim 1, wherein the plurality of the acoustic matching pieces are arranged in the arrangement direction and a direction perpendicular to the arrangement direction.

10. The ultrasound transducer according to claim 9, wherein each of the plurality of acoustic matching pieces has any shape of a polygonal column, a circular column, a polygonal cone, or a circular cone extending in a lamination direction of the plurality of acoustic matching layers.

11. The ultrasound transducer according to claim 10, wherein a filler consisting of resin is disposed between the plurality of acoustic matching pieces.

12. The ultrasound transducer according to claim 1, wherein a filler consisting of resin is disposed between the plurality of acoustic matching pieces.

13. The ultrasound transducer according to claim 12, wherein a filler consisting of resin is disposed between the plurality of acoustic matching pieces.

* * * * *